US008926903B2

(12) United States Patent
Nogami et al.

(10) Patent No.: US 8,926,903 B2
(45) Date of Patent: Jan. 6, 2015

(54) PRETREATMENT APPARATUS AND MASS SPECTROMETER EQUIPPED WITH THE SAME APPARATUS

(75) Inventors: Makoto Nogami, Tsuchiura (JP); Katsuhiro Kanda, Hitachinaka (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 636 days.

(21) Appl. No.: 13/060,164

(22) PCT Filed: Jul. 8, 2009

(86) PCT No.: PCT/JP2009/062767
§ 371 (c)(1),
(2), (4) Date: Mar. 21, 2011

(87) PCT Pub. No.: WO2010/026837
PCT Pub. Date: Mar. 11, 2010

(65) Prior Publication Data
US 2011/0157580 A1    Jun. 30, 2011

(30) Foreign Application Priority Data
Sep. 5, 2008   (JP) .................................. 2008-227717

(51) Int. Cl.
*G01N 1/28* (2006.01)
*G01N 1/40* (2006.01)
*G01N 30/00* (2006.01)

(52) U.S. Cl.
CPC .......... *G01N 1/405* (2013.01); *G01N 2030/009* (2013.01)
USPC .................... 422/67; 422/63; 422/64; 422/65; 436/47; 436/48; 436/49; 436/50; 436/174; 436/178; 250/288; 356/36; 435/286.1; 435/286.2; 435/286.3; 435/286.4; 435/287.1

(58) Field of Classification Search
CPC ......................... G01N 2030/009; G01N 1/405
USPC ............ 422/63–65, 67; 436/47–50, 174, 178; 250/288; 356/36; 435/286.1–286.4, 435/287.1
See application file for complete search history.

(56) References Cited

U.S. PATENT DOCUMENTS

| 2001/0001643 | A1 | 5/2001 | Simpson et al. |
| 2004/0181050 | A1 | 9/2004 | Shoji et al. |
| 2006/0255263 | A1* | 11/2006 | Ishimaru et al. ............... 250/288 |

FOREIGN PATENT DOCUMENTS

| EP | 1 159 597 B1 | 8/2007 |
| JP | 57-63434 A | 4/1982 |
| JP | 11-23546 A | 1/1999 |

(Continued)

*Primary Examiner* — Shogo Sasaki
(74) *Attorney, Agent, or Firm* — Mattingly & Malur, PC

(57) ABSTRACT

To perform accurate measurement in the analysis of chemical components with low concentration, pretreatment such as concentration and purification of samples is essential. For high-throughput of pretreatment of biological samples, various random clinical testing is encountered, where analytes change from sample to sample. The pretreatment apparatus has a separating agent selectively separating a specific component by allowing a sample solution to flow therethrough. A holding section holds a plurality of housing sections, which house the separating agent therein, and has an endless track. A pressurizing section applies pressure to the housing section in a continuous and random-accessible manner; and an extraction solution receiver mechanism selectively receives an extracted solution from the separating agent housed in the housing section. A mass spectrometer is that can be connected to the pretreatment apparatus. Thus, a large number of specimens can be simultaneously processed.

16 Claims, 7 Drawing Sheets

(56) References Cited

FOREIGN PATENT DOCUMENTS

| | | |
|---|---|---|
| JP | 11-125624 A | 5/1999 |
| JP | 11-160297 A | 6/1999 |
| JP | 11-201953 A | 7/1999 |
| JP | 2000-193670 A | 7/2000 |
| JP | 2002-531258 A | 9/2002 |
| JP | 2006-7081 A | 1/2006 |
| WO | 00/54023 A1 | 9/2000 |
| WO | 03/025170 A1 | 3/2003 |

* cited by examiner

FIG.2
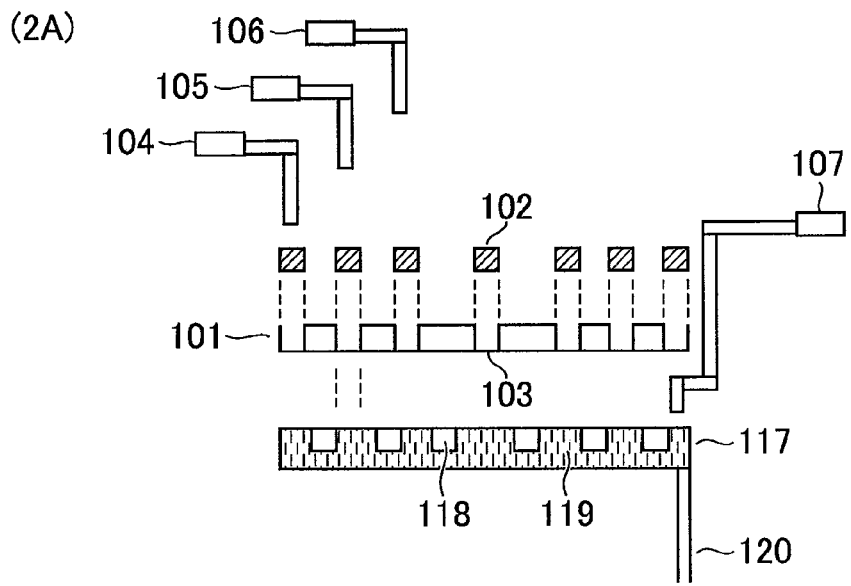
(2A)
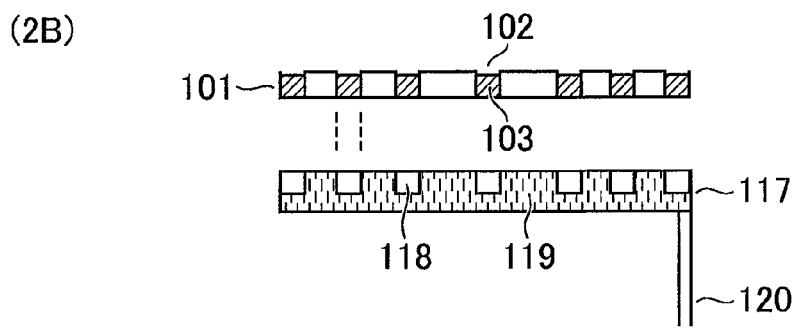
(2B)
2A ... FRONT VIEW AS VIEWED FROM A-A' PLANE OF FIG. 1
2B ... A VIEW ILLUSTRATING A DIFFERENCE BETWEEN IN VERTICAL POSITION BETWEEN THE SOLID-PHASE EXTRACTION CARTRIDGE 102, AND THE RECEIVER CONTAINER 118 AND THE WASTE RECEIVER 119 DUE TO A DIFFERENCE IN TURNING ANGLE BETWEEN THE CARTRIDGE TRANSFER MEANS 101 AND THE EXTRACTED SOLUTION RECEIVER MECHANISM 117.

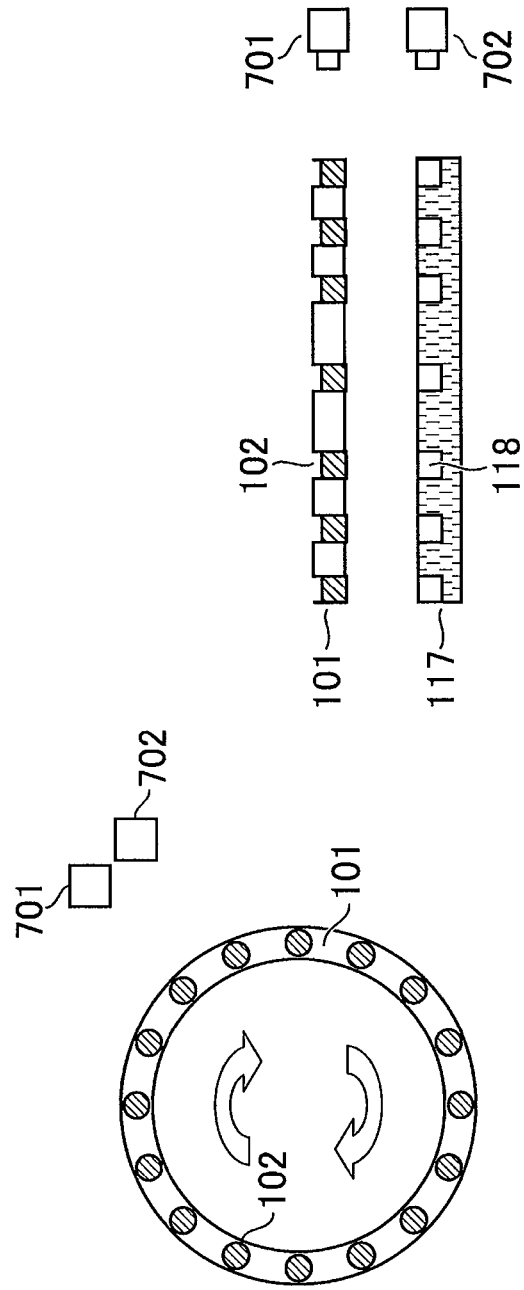
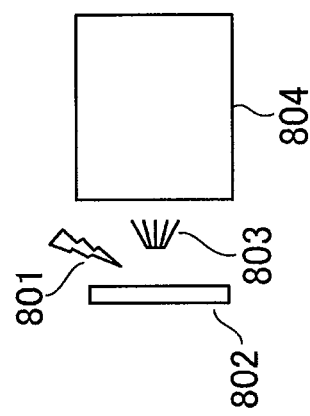

PRETREATMENT APPARATUS AND MASS SPECTROMETER EQUIPPED WITH THE SAME APPARATUS

TECHNICAL FIELD

The present invention relates to analyzing apparatus that automatically tests or analyzes a component contained in a specimen derived from a biological sample, such as blood, serum, plasma, cellular tissue, urine.

BACKGROUND ART

In analyzers for environment analysis and biological sample analysis in recent years, there is a growing need for quantitatively measuring a minute amount of analyte with high accuracy. In order to measure a minute amount of analyte accurately, it is not desirable to concurrently measure many kinds of components at one time. Further, it is necessary to concentrate components to be measured to some extent. Therefore, a pretreatment for concentrating and purifying a specimen is performed before analysis. A pretreatment method is here described by way of example in the case where particularly a specimen derived from a biological sample such as blood, serum, plasma, cellular tissue, or urine is tested and analyzed by instruments such as an automatic analyze.

There is known an automated pretreatment apparatus that employs an extraction treatment method using a solid-phase extraction plate in which, for example, a large number of wells are arranged on a single plate. For example, patent document 1 discloses an extraction treatment apparatus. In this apparatus, a reagent is aspirated and discharged by a dispensing head on which multiple syringes are arranged, to a solid-phase extraction plate on which 96 (12×8) wells are arranged in a matrix-like manner. The solid-phase extraction plate is positioned to above a vacuum rack by a movable X-Y-Z-positioning mechanism and depressurized for extraction treatment. Patent document 2 discloses a solid-phase extraction treatable apparatus which is provided with a sample rack to which 96 solid-phase extraction cartridges can be inserted. In addition, a passage through which liquid flow is provided by a pump is connected to the solid phase extraction cartridge from above and below the sample rack. As described in patent documents 3 and 4, a common pretreatment method for analyzing material derived from a biological sample involves using a separating column for separation and thereafter introducing a separated constituent into an analyzing section of an analytical instrument such as a mass spectrometer or a HPLC (high-performance liquid chromatography system).

Patent document 3 discloses an apparatus provided with a turntable into which 72 solid-phase extraction cartridges can be circularly inserted. The solid-phase extraction cartridge is positioned on the passages of two pumps by turning the turntable. A sample is eluted from a direction opposite the direction in which the sample is introduced into the cartridge. In this way, the degree of separation-degree is improved.

Patent document 4 discloses an apparatus as below. Cartridges can be arranged on a turntable having a plurality of cartridge housing portions. The cartridges are previously allowed to hold a minute amount of sample and thereafter the cartridges are manually set at the cartridge housing portions. The passage of an HPLC is connected to a cartridge in the turntable by turning the turntable. In this way, the spreading of the sample component in the column is reduced.

PRIOR ART REFERENCES

Patent Documents

Patent Document 1: JP-2006-7081-A
Patent Document 2: EP 1159597B1
Patent Document 3: JP-11-125624-A
Patent Document 4: JP-11-23546-A

SUMMARY OF THE INVENTION

Problem to be Solved by the Invention

For example, to pretreat a biological specimen before analysis by an automatic analyzer, high-throughput of pretreatment is needed and it is necessary to deal with analytical needs in clinical setting for various, randomly-demanded analytes, and emergency specimens that must be analyzed as quickly as possible even at the cost of delayed time for obtaining results for previous specimens whose analytical process have already started. In the treatment apparatus using the 96-well plate described in the patent document 1, a large amount of samples can be processed collectively with a uniform treatment. In contrast, when various multiple extraction methods with different solvents are necessary in the 96-well plate, corresponding to various analytes, the pretreatment efficiency and throughput decreases. This is because the multiple syringes provided in a single dispensing head disclosed therein cannot efficiently handle randomly-demanded analytes that require different reagents. Because different reagents need to be applied to each of the 96 wells, the merit of multiple syringes disappears, and the throughput decreases dramatically. That is, a plurality of reagents cannot be efficiently filled into the 96 wells by the multiple syringes, when the analytes to be analyzed are demanded randomly in the actual clinical setting. Thus, multiple extraction treatment using different solvents individualized for each of the 96 wells cannot be done with high-throughput. In the actual clinical testing, there will be various analytes, where the pretreatment method of one analyte is different from another. That is, with the device disclosed in the document 1, an amount of sample that can be pretreated with one single pretreatment is often not sufficient to fill a majority of the 96 wells, leading to inefficient use of the 96-well plate and the instrument; that is, it is likely that a majority of the 96 wells remain empty without samples, and that a plurality of such an operation with many empty wells must be repeated to process all the samples. That is, the efficiency and throughput decrease in the prior art.

Furthermore in this prior art, using a 96 well plate and a multiple-syringes head, pretreatment of a new set of samples cannot be started before a pretreatment of a preceding set of samples finishes, once one of the preceding pretreatment process steps has started. That is, it is difficult to efficiently perform the analytical pretreatment on various specimens coming into the clinical laboratory as they are demanded randomly.

In the patent documents 3 & 4, the disclosed turntable type pretreatment apparatus is quite inefficient, because each has only one mechanism for introducing a sample into an analytical LC column, limiting the throughput. After one set of solid-extraction pretreatment process is accomplished for one sample, the pretreated sample is introduced into the analytical column. After the HPLC analysis for the sample is finished, then pretreatment of another sample begins; that is, a pretreatment process and an LC analysis process are performed serially, not in parallel. Thus, the overall pretreatment and analysis efficiency is poor. In the HPLC methods described in the patent documents 2, 3 and 4, the extraction process can be done only in a closed fluid path where the fluid passage from the pump and the fluid passage through the cartridge or column to the detector are closed and continuous. Therefore, even if a plurality of the cartridges or columns are placed on the turntable, multiple pretreatment cannot be done simultaneously.

As described above, in the conventional pretreatment method for biological specimen, it is difficult to deal with the random, varying demands of analytes in various specimens in clinical laboratories, because it is difficult to pretreat various multiple specimens and analytes simultaneously in parallel; i.e., only one kind of pretreatment or only a single specimen pretreatment can be done at one time, leading to a poor treatment efficiency and a poor throughput capacity.

It is an object of the present invention to provide a pretreatment apparatus in which a multiple, parallel processing is available for simultaneous pretreatment of many kinds of specimens, with a system constructed to deal with various, random demands for clinical tests and analytes in clinical laboratories on the case-by-case basis. Further, it is another object of the invention to provide a mass spectrometer that can fully-automatically perform from pretreatment to detection by combining the above-mentioned pretreatment apparatus with the mass spectrometer.

Means for Solving the Problem

To achieve the above object, the configuration of the present invention is as follows:

A pretreatment apparatus includes: a separating agent separating a specific component from a specimen; a housing section housing the separating agent; a holding section holding a plurality of the housing sections; at least one pressurizing section applying pressure to the housing section placed on the holding section; a relative position changing mechanism changing a relative position between the holding section and the pressurizing section; a pressure holding section holding the pressure applied to the housing section; and an extraction solution receiver mechanism receiving a sample extracted from the housing section. In addition, an automatic analyzer includes an ionizing section ionizing an extraction sample obtained from the pretreatment apparatus; and a mass spectrometric section analyzing the sample ionized by the ionizing section.

The separating agent mentioned above may be anything if it has a function of selectively separating a specific chemical component in a sample by passing a sample solution to be tested therethrough. The general principle of selectively separating a specific component is as below. Substance that physically or chemically captures a specific component is used as a separating agent, which is generally a column type. In addition, the specific component captured is generally re-eluted by use of solvent. Other methods, e.g., separation using filters, may be applicable if the specific component can be separated. The relationship between the separating agent and the housing section can be variously conceived. For example, the separating agent and the housing section are united with each other, and the whole is disposed as waste after a single treatment. Alternatively, a used separating agent is removed from the whole after multiple treatments, where the timing of removal depends on a condition of the separating agent. And after the removal of used separating agent, new separating agent is introduced into the housing by a dispensing method. However, any structure may be applicable for the housing of the separating agent. The holding section can be enhanced in operability by being positioned along an endless track on such surface as a rotatable circular or oval disk. In this way, the pressurizing section can be shared by a large number of the housing sections. In other words, the provision of one pressurizing section can simultaneously pre-treat multiple specimens in parallel. It is conceivable that a plurality of the pressurizing sections are arranged depending on the number of the housing sections provided on the holding section. In such a case, it is desirable that the pressurizing section be set so that the center of the force applied from the pressurizing section may coincide in position with the gravity center of the holding section. Specifically, if the even numbers of the pressurizing sections are provided, they are arranged line-symmetrically with respect to the gravity center of the holding section to prevent the breakage of the holding section. If the odd numbers of the pressurizing sections are provided, they are arranged symmetrically with respect to the gravity center of the holding section to prevent the breakage of the holding section. The pressure holding section holding the pressure applied into the housing section may be anything if it has a function of keeping the pressure inside the cartridge, equipped with such component as a one-way valve or check valve. The extraction solution receiver mechanism receiving the extraction sample extracted from the cartridge may have a structure integral with or separate from the cartridge.

The pretreatment apparatus described above can be used in combination with a variety of analyzers. For example, the pretreatment apparatus can be combined with a mass spectrometer, which measures a mass-to-charge ratio of the sample as described below. The mass spectrometer accelerates ionized sample and measures a difference of ion trajectory, or a difference in flight time, which is determined by a mass-to-charge ratio of the sample ion. In such a case, a piping or a tube is provided which is adapted to introduce the extraction solution collected by the extraction solution receiver mechanism, into an ion source of the mass spectrometer.

Effect of the Invention

According to the present invention, the holding section has the endless track and the housing section has the mechanism keeping the pressure applied thereto.

Therefore, a large number of specimens can be simultaneously pre-treated, such as extracted and concentrated. Thus, the time of pretreatment can be significantly reduced. Further, the automatic analyzer can be provided that can fully-automatically perform from the pretreatment of a specimen to the mass spectrometric analysis of a sample by having the mechanism introducing the specific component extracted from the above-mentioned pretreatment apparatus into the detecting section such as a mass spectrometer.

BRIEF DESCRIPTION OF THE DRAWINGS

FIG. 2 is a front view illustrating the schematic configuration of the automatic mass spectrometer according to the embodiment of the present invention.

FIG. 7 is a schematic view of a liquid-level sensing function.

FIG. 8 illustrates an alternative of the detecting section (first).

MODE FOR CARRYING OUT THE INVENTION

Figure 1:
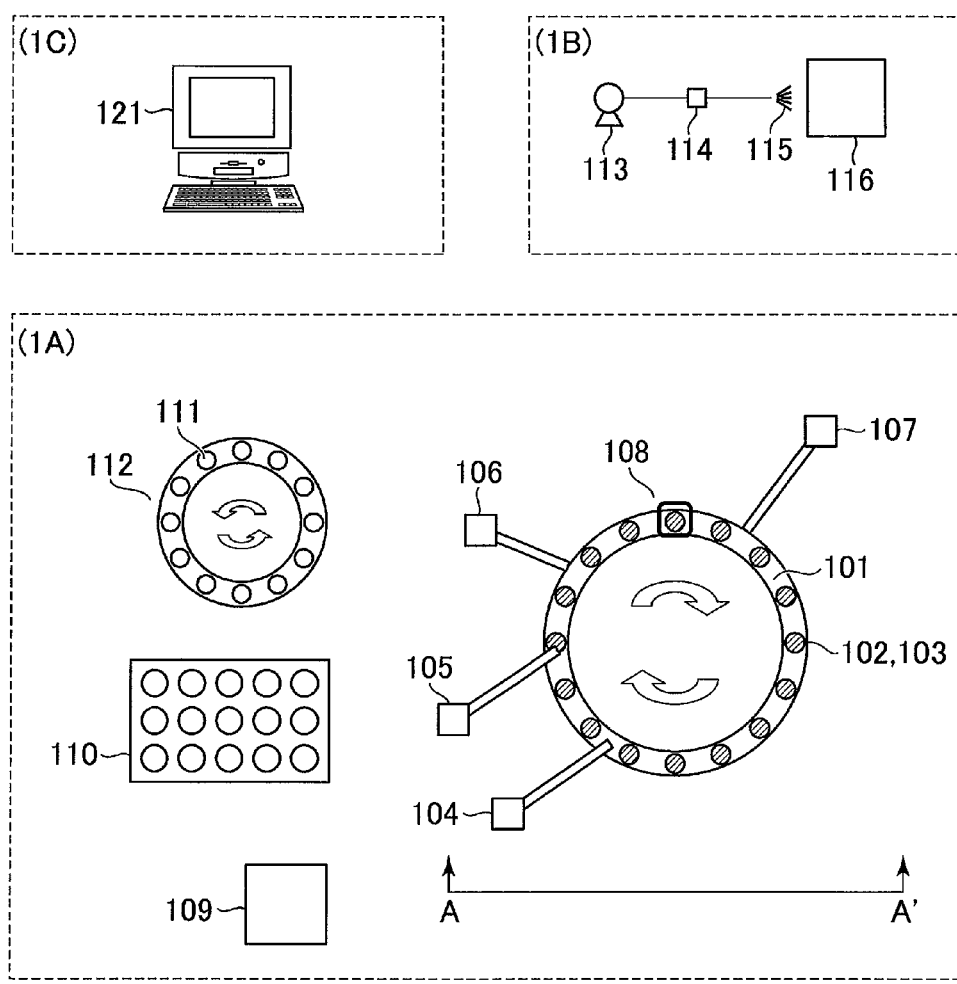
FIG. 1 is a plan view illustrating a schematic configuration of an automatic mass spectrometer according to an embodiment of the present invention.

An embodiment of an automatic analyzer according to the present invention will be described in detail with reference to the drawings. As the embodiment is an example of the present invention, the present invention is not limited thereto.

In the field of automatic analysis of biological samples, widely used analyzing methods are a colorimetric biochemical assay method and an immunoassay analytical method. In the colorimetric biochemical assay method, a reagent that reacts with a target component in a sample to change its color is used and the change of color is measured for analysis by a multiple wavelength photometer. In the immunoassay analytical method, a substance that specifically reacts with a target component by use of antigen-antibody reaction is used as a reagent and the amount of the substance specifically reacting with the target component is measured for analysis. In addition to these two analyzing methods, to measure components with lower concentration, a mass spectrometer is increasingly used as a detector in recent years. One major application is monitoring of drug concentration in blood, or therapeutic drug monitoring (TDM), for observing pharmacokinetic characteristics of therapeutic drugs in patients to individually optimize drug therapy. When a therapeutic drug is administered to a patient, in order to ensure effectiveness and safety, it is important to individually make a dosage schedule in accordance with each patient's pharmacokinetic characteristic and specific clinical symptoms of a patient to be therapeutically treated. Even if the same amount of therapeutic drug is dosed, a treatment effect may be different depending on each individual patient, because there is a difference in blood concentration depending on the individual variation in the drug metabolism in each patient's body. For this reason, a technology of optimizing an amount and frequency of drug administration, so as to allow the blood drug concentration of an individual patient to be controlled within a therapeutic range of concentration by measuring the blood concentration of the drug, i.e., TDM, is carried out. Measurement of concentration of a drug in blood for the TDM requires such measurement sensitivity as to be clinically satisfied with a small amount of blood sample, in addition to promptness and ease of measurement. Therefore, immunoassay analysis method is widely used. However, immunoassay analysis needs readily-available antibody for a drug; therefore, it has the following drawbacks: testing cost is expensive; there is cross-reaction with an analogous compound such as a metabolite of the therapeutic drug; and, above all, it cannot be applied to a therapeutic drug for which there is no available antibody. Thus, in recent years, there is a new physical-chemical detection approach in which therapeutic drug monitoring is performed by using a mass spectrometer as a detector.

If the mass spectrometer is used as a detector, high-temperature and/or high-voltage is applied to a sample for evaporation and ionization in an ionizing device section in an upper-stream portion of the mass spectrometer, and the ionized sample is introduced into the mass spectrometer. However, several tens of thousands of, or more, kinds of components exist in a specimen derived from a biological sample such as blood or urine. If many kinds of components are simultaneously ionized, the obstruction of ionization (i.e., ion suppression) occurs. It is therefore difficult to perform accurate detection. Thus, pretreatment to concentrate and purify a sample becomes necessary before a sample is introduced into the mass spectrometer.

FIG. 1 is a plan view of an automatic analyzer according to the present embodiment. FIG. 2 is a front view as viewed from A-A' of FIG. 1. The automatic analyzer according to the present embodiment includes a solid-phase extraction section (1A), a detecting section (1B) and a control section (1C) in FIG. 1.

The solid-phase extraction section (1A) includes a holding section, cartridge transfer means (101), on which housing sections, as cartridge holding containers (103), are arranged. The cartridge holding containers (103) can each hold a separating agent, such as a corresponding solid-phase extraction cartridge (102), that can be used in a disposable manner. The solid-phase extraction section (1A) includes a cartridge storing section (109) which is capable of storing the separating agents, such as the solid-phase extraction cartridges (102). The solid-phase extraction section (1A) includes a turning arm (104) capable of transferring the solid-phase extraction cartridge (102) from the cartridge storing section (109) to each cartridge holding container (103) or housing section. The solid-phase extraction section (1A) includes a turning arm (105) capable of transferring a sample to the solid-phase extraction cartridge (102) or separating agent from a specimen transfer section (110) which transfers specimens into the apparatus. The solid-phase extraction section (1A) includes specimen transfer means (112) on which specimen containers (111) are arranged. The solid-phase extraction section (1A) includes a turning arm (106) capable of transferring a reagent from the specimen container (111) to the solid-phase extraction cartridge (102). The solid-phase extraction section (1A) includes a pressurizing section (108) capable of performing an extraction step by applying pressure to at least one solid-phase extraction cartridge (102). The solid-phase extraction section (1A) includes an extraction solution receiver mechanism (117) where a plurality of receiver containers (118), which are arranged below the specimen transfer means (112), a waste receiver (119) are capable of receiving waste, and a waste port (120). The receiver containers (118) can receive solution extracted from the solid-phase extraction cartridges (102). The solid-phase extraction section (1A) includes a turning arm (107) capable of transferring the extracted solution from the receiver container (118) to a sample introducing section (114).

The detecting section (1B) includes: a pump (113) which pushes solution to introduce a sample into an ionizing section; the ionizing section (115) which ionizes the sample by application of voltage; a sample introducing section (114) located downstream of the pump (113) and upstream of the ionizing section (115) and adapted to introduce the pretreated sample into a fluid passage; and a mass spectrometric section (116) which analyzes and measures the ionized sample.

A control section (10) is comprised of a controller (121) that can simultaneously control all parts constituting the apparatus automatically.

The testing and analysis procedures of the apparatus, including solid-phase extracting operation, is described in detail in order of the procedure steps. The present embodiment describes an example of a mode of embodiment where the positions of cartridges are shifted. However, other embodiments are also possible where other modes of position control are used, such as a position control of a pressurizing mechanism by rotation movement, or by an X-Y translational movement. In the present embodiment where a cartridge disk is turned, an effect of simplifying a configuration can be expected. However, moving the pressurizing mechanism facilitates the change of the order of pressurization, from which we can expect an improvement in the random accessibility of the pretreatment.

[Standard Reagent Addition Step]

An internal standard reagent is first added to a sample transferred to the apparatus by the specimen transfer section 110. In this addition, the internal standard reagent in a reagent container in the specimen transfer means 112 is aspirated by the turning arm 105 and is added to the specimen in the specimen transfer section 110. The internal standard reagent uses a stable-isotope-exchanged compound, which is obtained by exchanging one or more of the atoms to stable isotopes in the molecular formula of the target analyte; e.g., exchanging hydrogen atoms (H) to deuterium atoms (D), or exchanging carbon 12 atoms ($^{12}C$) to carbon 13 ($^{13}C$) isotopes. Alternatively, the internal standard reagent uses a compound whose chemical and physical characteristics are analogous to a target analyte. The turning arms 105, 106 and 107 are each provided at a tip end with a pipette or a syringe capable of aspiration and discharge of the reagents or the sample. In addition, the turning arms 105, 106 and 107 are each provided with a mechanism that can automatically wash the tip end after the aspiration or discharge of the reagents or the sample.

The solid-phase extraction cartridge in the present embodiment employs a method in which a specific component captured by use of substance physically or chemically reacting is re-eluted by use of solvent. However, the solid-phase extraction cartridge may use other methods if the specific component can be separated. For example, another method is also conceivable in which components having a specific size are removed by a filter.

[Mounting and Dismounting of Solid-Phase Extraction Cartridge 102]

The cartridge holding containers 103 are equally separated from one another at a same angle with respect to the center in the cartridge transfer means 101. The solid-phase extraction cartridges 102 are replaceable for each treatment. A cartridge replacing mechanism not illustrated in the figure dismounts the solid-phase extraction cartridge that has been used and transfers a new solid-phase extraction cartridge to an unoccupied solid-phase extraction cartridge holding container 103 on the cartridge transfer means 101. Unused solid-phase extraction cartridges are stored in the solid-phase extraction cartridge storing section 109, sequentially transferred by the turning arm 104 and set in the corresponding cartridge holding containers 103. The solid-phase extraction cartridges 102 may also be set in the corresponding cartridge holding containers 103 by transfer means having a limited track such as a belt conveyor. It may be conceivable that only a separating column inside the solid-phase extraction cartridge, but not the cartridge itself, is replaced for each treatment. In such a case, the used column is removed from the solid-phase extraction cartridge by a column-replacing mechanism not illustrated in the figure. A new column is housed into the emptied solid-phase extraction cartridge by a dispensing method. The cartridge per se can be repeatedly used for each treatment, which results in a reduction in operational cost.

Another scheme is possible in which the solid-phase extraction cartridge or the column are allowed to drop from above the cartridge transfer means 101 down into the cartridge holding container or into the cartridge and be received and housed therein.

[Washing Step of the Solid-Phase Extraction Cartridge 102]

The solid-phase extraction cartridge 102 is next washed. A washing step is performed as below. The cartridge transfer means 101 is rotated into the action range of the turning arm 106. The turning arm 106 aspirates a wash reagent in a sample container in the specimen transfer means 112 and injects it into the solid-phase extraction cartridge 102. The cartridge transfer means 101 is turned into the action range of the pressurizing section 108. Pressure is applied to the cartridge, so that the wash reagent is moved from the upper portion to lower portion of the solid-phase extraction cartridge 102 for the washing step. The wash solution generally used is an organic solvent such as methanol, or acetonitrile. The present embodiment uses a 100%-methanol solution. The extraction solution receiver mechanism 117, having the same shape as the cartridge transfer means 101, is disposed under the cartridge transfer means 101. Depending on the turning angles of the cartridge transfer means 101 and of the extraction solution receiver mechanism 117, either the receiver containers 118 or the waste receivers 119 is alternately positioned directly under the cartridge holding container 103. Its state is shown in FIGS. 2A and 2B in FIG. 2. In the washing step, the waste receiver 119 is disposed directly under the cartridge holding container 103. The wash solution is moved to the lower portion of the solid-phase extraction cartridge 102, and then passes through the waste receiver 119, and is discarded from the waste port 120. Both the cartridge transfer means 101 and the extraction solution receiver mechanism 117 are provided with rotation mechanisms which can turn both clockwise and counterclockwise, so that they can be turned in such a direction as to be shiftable to the next operational position in the shortest time.

A plurality of the solid-phase extraction cartridges 102 are arranged on the cartridge transfer means 101. It is possible to simultaneously perform the aspiration and injection operations of the reagents and samples, and the pressurizing operation on the solid-phase extraction cartridges 102. The positional relationship between the shape of the cartridge transfer means 101 and the cartridge holding containers 103 is such that the cartridge holding containers 103 are equally separated from one another by a same angle with regard to the center of the circular cartridge transfer means 101. It is also possible that the shape of a turntable is elliptical. It is also possible that the plurality of cartridge holding containers 103 are not separated from one another by a same angle with regard to the center of the cartridge transfer means 101.

Figure 6:
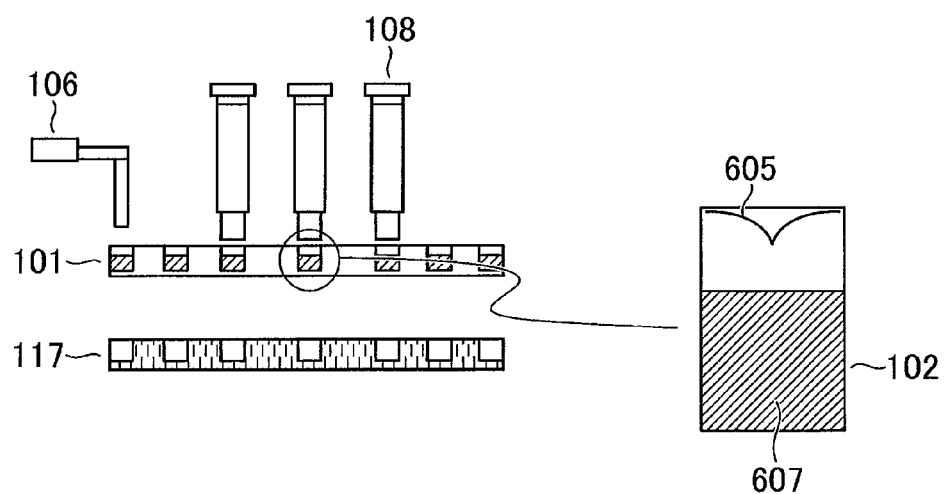
FIG. 6 is a schematic view of a solid-phase extraction cartridge provided with a valve function.

The system of the pressurizing section 108 is here described. In order to allow an extraction column 607 in the solid-phase extraction cartridge 102 to adsorb or elute a sample, it is necessary to allow the sample and a reagent to be in contact with the extraction column 607 for a certain amount of time. For example, a time necessary for liquid to pass through 1 cc of extraction column is about one minute. In contrast, the time taken to inject the sample and the reagent into the solid-phase extraction cartridge 102 is several seconds. Therefore, if the pressurizing section 108 exists at only one location, throughput decreases. For this reason, the pressurizing section and the turning arm 106 used to inject reagents are provided at a plurality of locations. In addition, the cartridges are installed on the turntable having random accessibility. In this way, it is possible to process a plurality of samples and analytes at the same time to achieve an improvement in throughput. A provision of a mechanism capable of maintaining pressure for a given length of time even after the pressure is once applied can achieve an improvement in throughput. FIG. 6 is a schematic diagram illustrating an example of a solid-phase extraction cartridge which is equipped with a lid having a one-way valve function provided at an opening section of the cartridge. The solid-phase extraction cartridge 102 illustrated in FIG. 6 is provided at an upper portion with a valve lid 605 having a one-way valve function. The pressurizing section 108 can keep the pressure applied to the inside of the solid-phase extraction cartridge 102. With these mechanisms, it is possible to simultaneously perform the aspiration and injection operations of a sample and a reagent, and the pressurizing operation on the solid-phase extraction cartridge 102 while turning the cartridge transfer means 101. Thus, throughput can be improved.

Figure 4:
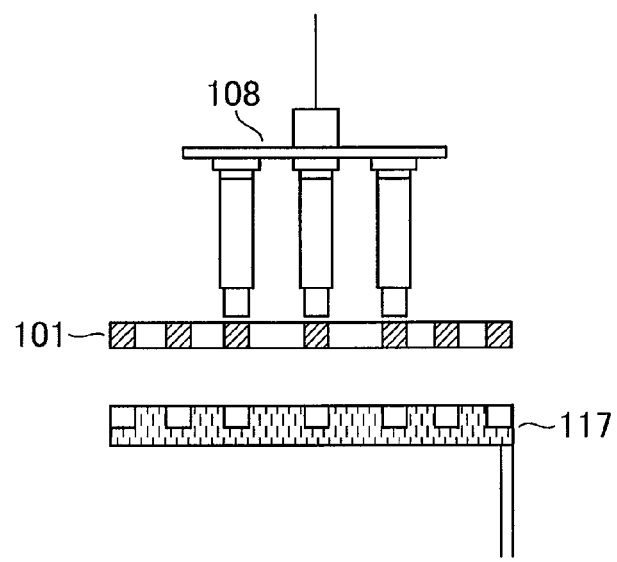
FIG. 4 is a front view of a pressurizing section in the case where the pressurizing section is of a positive-pressurizing type.
Figure 5:
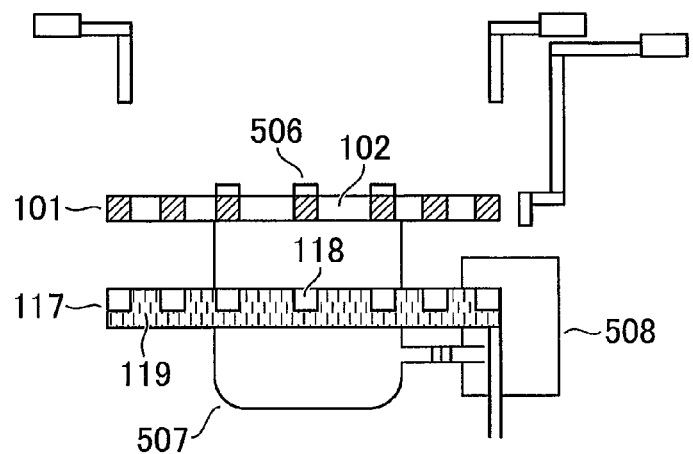
FIG. 5 is a front view of the pressurizing section in the case where the pressurizing section is of a depressurizing type.

FIG. 4 is a front view of the pressurizing section, which is of a positively pressurizing type. The solution injected into the solid-phase extraction cartridge 102 cannot move from the upper portion to lower portion of the solid-phase extraction cartridge 102 solely by its own weight because of the fluid-flow resistance of the extraction column in the solid-phase extraction cartridge 102. Therefore, after the solution is injected into the solid-phase extraction cartridge, it is necessary to apply pressure to the solution to promote the penetration of the solution into the column. In the present embodiment, the pressurizing section 108 is provided on the upper portion of the cartridge transfer means 101. The cartridge is pressurized from the upper portion of the solid-phase extraction cartridge 102 by a pump to promote the passing of the solution into the solid-phase extraction cartridge. In applying pressure to the inside of the cartridge, a support is provided on the lower portion of the turntable in order to prevent the turntable from being damaged by the pressure applied to the turntable. Similarly, in order to prevent the turntable from being damaged by the pressure applied thereto, it is conceivable that a plurality of pressurizing sections are arranged at positions symmetrical to each other with respect to the center of the turntable so that pressure is equally applied to the turntable vertically from the upper portion thereof. FIG. 5 illustrates the case where the pressurizing section is of a depressurizing type. The pressurizing section is provided with a vacuum rack 507, a vacuum pump 508 and a lid 506. The pressurizing section is provided with a mechanism that depressurizes the solid-phase extraction cartridge 102, a receiver container 118 and a waste receiver 119 during the depressurization process. In the depressurized state, reagents and a samples are moved from the upper portion to the lower portion of the solid-phase extraction cartridge 102 for the passing-through thereof.

[Equilibrating Step of the Solid-Phase Extraction Cartridge 102]

After the solid-phase extraction cartridge 102 is washed once with an organic solvent, the separating agent is equilibrated so that a target component in the sample component can be adsorbed to the separating agent in the solid-phase extraction cartridge 102. In the equilibrating step, the specimen transfer means 112 is turned into the action range of the turning arm 106. An equilibrating reagent in a reagent container in the specimen transfer means 112 is aspirated by the turning arm 106 and injected into the solid-phase extraction cartridge 102. The cartridge transfer means 101 is turned into the action range of the pressurizing section. Pressure is applied to the equilibrating reagent, which is moved from the upper portion to lower portion of the solid-phase extraction cartridge 102. In this way, the equilibrating step is performed. An equilibrating solution generally used is an aquatic solution. The present embodiment uses a solution of 100% water. In the equilibrating step, the waste receiver 119 is disposed under the cartridge holding container 103. The wash liquid is moved to the lower portion of the solid-phase extraction cartridge 102, and then passes through the waste receiver 119 and is discarded from the waste port 120.

[Adsorption Step of Introducing Sample to the Solid-Phase Extraction Cartridge]

The sample added with the internal standard reagent is injected into the solid-phase extraction cartridge 102, which have been subjected to the equilibration to perform the adsorption of a target component in the specimen. In the adsorption step, the specimen transfer section 110 is moved into the action range of the turning arm 105. The turning arm 105 aspirates a sample from the inside of the specimen transfer section 110 and discharges it into the upper portion of the solid-phase extraction cartridge 102. The cartridge transfer means 101 is turned into the action range of the pressurizing section, where pressure is applied to the solid-phase extraction cartridge 102 to move the sample from the upper portion to lower portion of the solid-phase extraction cartridge 102. In this way, the adsorption step is performed. In the adsorption step, the waste receiver 119 is disposed under the cartridge holding container 103. The components in the sample that is not absorbed to the solid-phase extraction cartridge 102 move together with the solution that move to the lower portion of the solid-phase extraction cartridge 102, and then passes through the waste receiver 119, and is discarded from the waste port 120.

Alternatively, a component other than the target component in the sample may be adsorbed in the adsorption step and the target component may be received in a receiver under the cartridge holding container 103. In such a case, since a step required for the extraction step is simplified, the extraction can be done in a short time. As described earlier, it is conceivable that an extraction method such as a filter other than the column is used.

[Liquid Level Sensing Mechanism]

A liquid level sensing mechanism is here described. FIG. 7 is a schematic view of the liquid level sensing mechanism. Samples may be different from each other in property such as viscosity. Therefore, when a sample is adsorbed to a solid-phase extraction column, the extraction cannot be uniformly done even if the same pressure is applied. For this reason, a CCD camera 1 (701) is disposed outside the cartridge transfer means 101. While sequentially turning the cartridge transfer means 101, the liquid level of each of the solid-phase extraction cartridge 102 is observed. If the liquid does not sufficiently permeate the column, the cartridge transfer means 101 is turned into the action range of the pressurizing section and pressure is applied to the solid-phase extraction cartridge 102 again. A CCD camera 2 (702) on the outside of the extraction solution receiver mechanism 117 is provided with the same mechanism. While turning the extraction solution receiver mechanism 117, the liquid level in the receiver container is sensed. Both or one of the CCD camera 1 (701) and the CCD camera 2 (702) may be used to sense the liquid level. It is also possible to use a mechanism generally used to sense a liquid level other than the liquid level sensing mechanism using the CCD camera, so as to improve the reproducibility of solid-phase extraction.

[Washing Step to Remove Unnecessary Component in the Column]

The sample component adsorbed to the solid-phase extraction cartridge 102 in the adsorption step is subjected to a washing step, so that components other than the target component that is non-selectively adsorbed are desorbed from the solid-phase extraction cartridge 102. In this way, the target component becomes concentrated. In the washing step, the specimen container 111 is turned into the action range of the turning arm 106. The turning arm 106 aspirates the wash reagent in the reagent container in the specimen container 111 and discharges it on the cartridge transfer means 101, i.e. injects it into the solid-phase extraction cartridge 102. The cartridge transfer means 101 is turned into the action range of the pressurizing section, where pressure is applied to the solid-phase extraction cartridge 102 to move the wash reagent from the upper portion to lower portion of the solid-phase extraction cartridge 102. In this way, the washing step is carried out. The wash solution generally uses a solution containing an organic solvent such as methanol, or acetonitrile. The present embodiment employs a 5%-methanol solution. In the washing step, the waste receiver 119 is disposed under the cartridge holding container 103. The washing liquid is moved to the lower portion of the solid-phase extraction cartridge 102, and then passes through the waste receiver 119, and is discarded from the waste port 120.

[Target Component Elution Step]

Elution of the target constituent adsorbed to the solid-phase extraction cartridge 102 is carried out.

Similarly to the washing step, the elution step is performed as below. An elution reagent is injected into the solid-phase extraction cartridge 102, where pressure is applied to the solid-phase extraction cartridge 102 to move the elution reagent from the upper portion to the lower portion of the solid-phase extraction cartridge 102. The elution reagent generally used is an organic solvent such as methanol, or acetonitrile. The present embodiment employs a 1000-methanol solution. In the elution step, the receiver container 118 is disposed vertically under the cartridge holding container 103 in accordance with the turning angles of the cartridge transfer means 101 and of the extraction solution receiver mechanism 117. The elution solution is moved to the lower portion of the solid-phase extraction cartridge 102, and then is injected into the receiver container 118.

[Ionization Reagent Addition Step]

Figure 3:
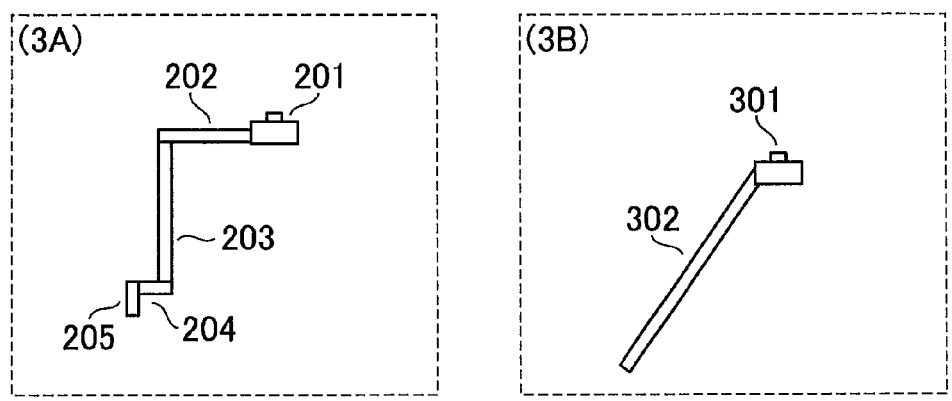
FIG. 3 is a front view of a turning arm used in the embodiment of the present invention.

The extraction reagent extracted in the elution step is aspirated and discharged by the turning arm 107 and transferred to the sample introducing section adapted to introduce a sample into a flow passage. FIG. 3A is a front view of the turning arm 107. The turning arm 107 is used to aspirate the sample from the receiver container 118 and inject it into the sample introducing section. The turning arm 107 is shaped such that a member 1 (202) is disposed to extend horizontally from a fixed shaft 201, a member 2 (203) is disposed to extend vertically from the distal end of the member 1 (202), a member 3 (204) is disposed to extend horizontally from the distal end of the member 2 (203), and a member 4 (205) is disposed to extend vertically from the distal end of the member 3 (204). The distal end of the member 4 (205) is provided with a syringe or a syringe tip, and thereby solution can be aspirated and discharged. The receiver container 118 is secured to the extraction solution receiver mechanism 117, above which the cartridge transfer means 101 is disposed. In this way, the turning arm 107 is shaped to be movable between the cartridge transfer means 101 and the extraction solution receiver mechanism 117. FIG. 3B illustrates an alternative of the turning arm 107. This turning arm is such that a member 1 (302) is disposed to extend obliquely from the fixed shaft 301. The distal end of the member 1 (302) is provided with a syringe or a syringe tip, and thereby solution can be aspirated and discharged. This turning arm is configured more simply than the turning arm 3A, so that it can be manufactured inexpensively. It is conceivable that, instead of the turning arm, a piping structure is used to introduce an extraction sample into the sample introducing section.

The sample introduced into the ionizing section 115 is ionized in the state in which such a sample has electrical charge of [M+H$^+$] resulting from the addition of a proton [H$^+$] to a component [M] under high-temperature or high-voltage, and introduced into the mass spectrometric section 116. The ionizing section essentially needs the state in which there exist many proton charges. Therefore, an ionization reagent is added to the extracted solution, in which the target analyte component has been concentrated by the solid-phase extraction cartridge 102. The ionization reagent generally used is an organic acid such as a formic acid or an acetic acid. In the present embodiment, a formic acid solution is added to provide a concentration of 0.1% after the addition.

[Introduction Step into the Detecting Section]

The sample added with the ionization reagent is introduced into the detecting section 1B, in which measurement and analysis are performed. The introduction of the sample into the detecting section 1B is such that the extraction solution receiver mechanism 117 is rotated into the action range of the turning arm 107 and the sample is aspirated from the receiver container 118 and is injected into a sample introduction port.

Figure 9:
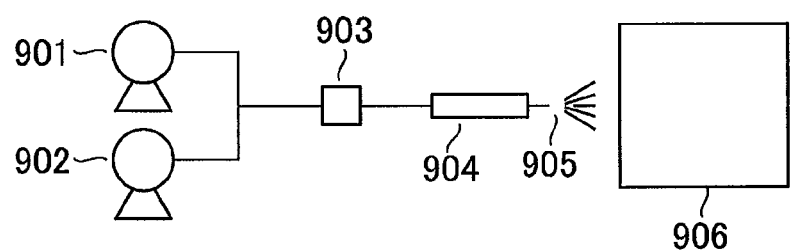
FIG. 9 illustrates an alternative of the detecting section (second).
Figure 10:
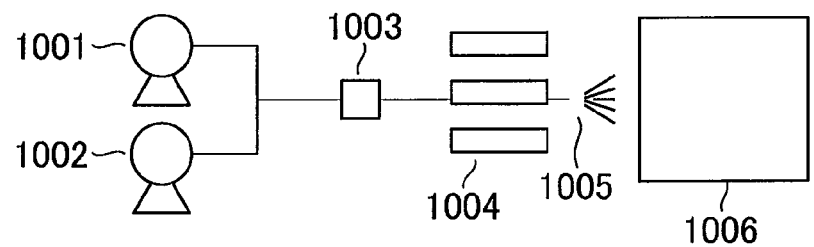
FIG. 10 illustrates an alternative of the detecting section (third).

In the present embodiment, the ionizing section 115 uses electro-ion spray ionization (ESI) or atmospheric pressure chemical ionization (APCI). FIG. 8 illustrates a configurational view of a first alternative of the detecting section. It is possible that the ionizing section uses a matrix-assisted laser desorption ionization (MALDI) in which ionization is performed by a MALDI plate 802 and a laser beam 801. FIG. 9 illustrates a configurational view of a second alternative of the detecting section. A configuration is possible in which a separation column 904 is disposed in rear of a sample introduction port 903 and in front of an ionizing section 905. Even when accurate measurement may be difficult because many impurities are contained in addition to the target component, accurate measurement is made possible with this configuration, since a sample is separated by the separation column 904 before the measurement. With this separation column, the number of components introduced into the mass spectrometer per unit time is reduced. Thus, the accurate measurement can be achieved. A reversed-phase column, a normal-phase column, a cation exchange column, an anion exchange column is used as the separation column 904. The eluents of a pump 1 (901) and of a pump 2 (902) are appropriately selected in accordance with the separation column employed and components are separated while applying temporal gradient to the mixture ratio of the two eluents. FIG. 10 illustrates a configurational view of a third alternative of the detecting section. In order to increase throughput, this alternative is configured such that separation columns 1004 are arranged in a revolver-type configuration, in a multiplexed manner. An ionizing section 1005 and a separation column 1004 are brought into connection in a series at the time synchronous to the elution time of a target drug eluting from the separation column 1004. In this way, the washing and equilibrating of the separation columns are done simultaneously in a multiplexed manner among the multiple separation columns. This can increase throughput.

[Configuration of the Control Section]

Figure 11:
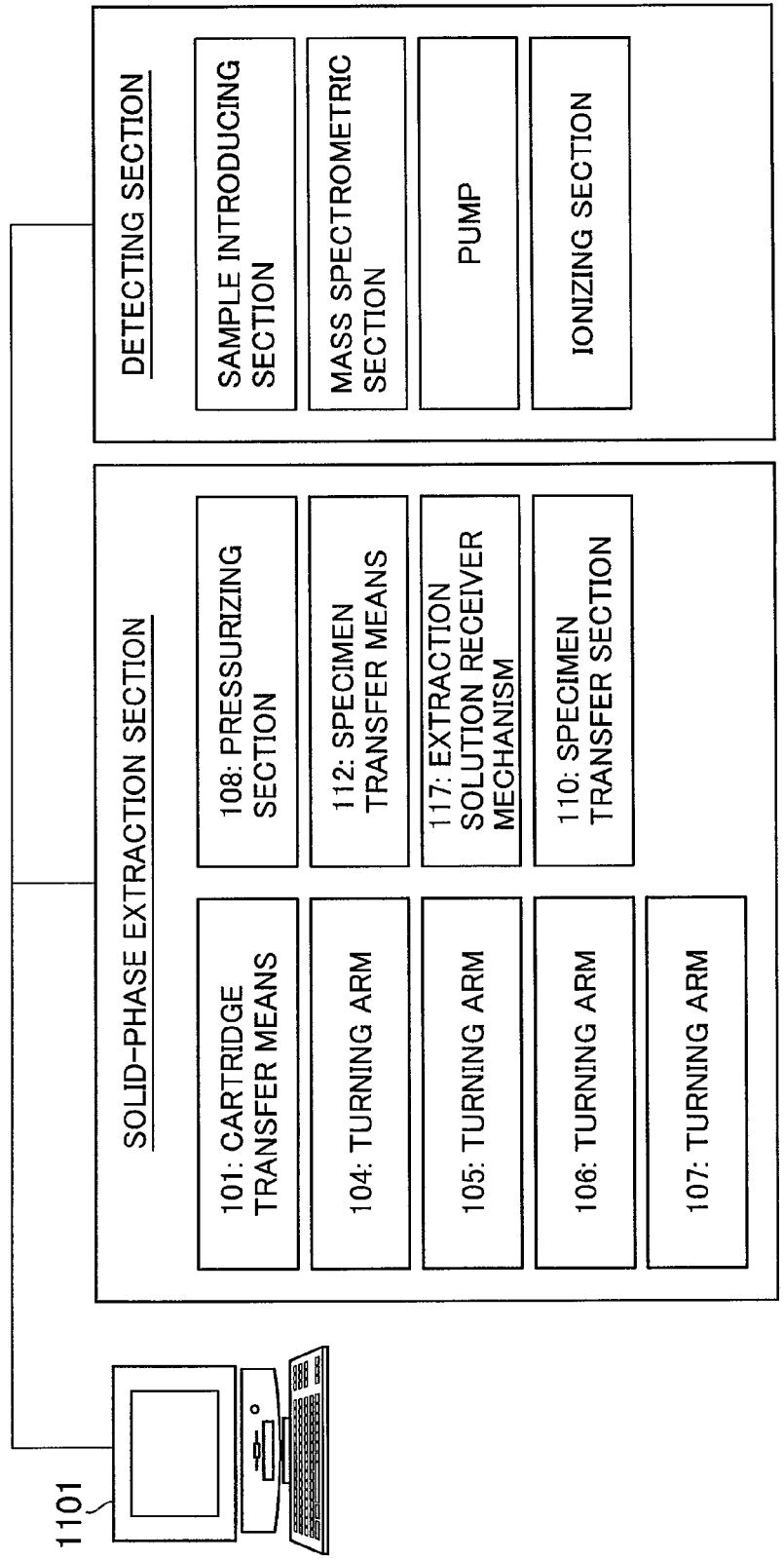
FIG. 11 illustrates a method of controlling a solid-phase extraction section and a detecting section by a control device.

FIG. 11 illustrates a control method by use of a controller 121. The controller 121 can process the cartridge transfer means 101, the turning arm 104, the turning arm 105, the turning arm 106, the turning arm 107, the pressurizing section 108, the specimen container 111, the specimen transfer means 112, the cartridge storing section 109, the sample introducing section 114, the mass spectrometric section 116, the pump 113 and the ionizing section 115, which constitute the present apparatus. Since a series of the steps can be automatically processed, the overall processing time can be efficiently controlled.

DESCRIPTION OF THE REFERENCE NUMERALS

101 . . . Cartridge transfer means
102 . . . Solid-phase extraction cartridge
103 . . . Cartridge holding container
104 to 107 . . . Turning arms
108 . . . Pressurizing section
109 . . . Cartridge storing section
110 . . . Specimen transfer section
111 . . . Specimen container
112 . . . Specimen transfer means
113 . . . Pump
114 . . . Sample introducing section
115 . . . Ionizing section
116 . . . Mass spectrometric section
117 . . . Extraction solution receiver mechanism
118 . . . Receiver container
119 . . . Waste receiver
120 . . . Waste port
121 . . . Controller

The invention claimed is:

1. A pretreatment apparatus comprising:
a solid-phase extraction cartridge for separating a specific component from a sample solution;
a cartridge holding container for housing the solid phase extraction cartridge;
a cartridge transfer means for holding a plurality of the cartridge holding containers;
a sample solution injection mechanism for injecting the sample solution into a selected one of said plurality of cartridge holding containers;
a reagent injection mechanism for injecting a reagent into said selected one of said plurality of cartridge holding containers;
a pressurizing section for applying pressure to said selected one of the plurality of cartridge holding containers;
a pressure holding section for holding the pressure applied to said selected one of the plurality of cartridge holding containers from the pressurizing section,
an extraction solution receiver mechanism for receipt of the specific component separated from the sample solution by said solid-phase extraction cartridge;
whereby said sample solution injection mechanism, said reagent injection mechanism and said pressurizing section are arranged with respect to said cartridge holding means so that said sample solution injection mechanism, said reagent injection mechanism and said pressurizing section can process and can operate with at least two of said plurality of cartridge holding containers being held by said cartridge transfer means, and
a control section, including a controller configured for simultaneously controlling all parts of the pretreatment apparatus automatically and including controlling at least two of a change of a position of the cartridge transfer means to change a relative position between said cartridge transfer means and said pressurizing section, to change a relative position between said cartridge transfer means and said sample solution injection mechanism, to change a relative position between said cartridge transfer means and said reagent injection mechanism, and a relative position between said cartridge transfer means and said extraction solution receiver mechanism, whereby said at least two of said plurality of said cartridge holding containers to be operated and processed can be simultaneously changed, said control section controller further being configured for controlling the operation of the cartridge transfer means, the sample solution injection mechanism, the reagent injection mechanism and the pressurizing section.

2. The pretreatment apparatus according to claim 1 further including a relative position changing mechanism for changing the relative position between the cartridge transfer means and the pressurizing section.

3. The pretreatment apparatus according to claim 2, wherein the pressure holding section comprises a valve lid provided at an upper portion of each cartridge holding container, said valve lid having a one way valve structure, the pressure holding section being shifted by the relative position changing mechanism, and holding pressure in the selected one of the plurality of cartridge holding containers while the pressurizing section does not apply the pressure thereto.

4. The pretreatment apparatus according to claim 2, wherein the extraction solution receiver mechanism comprises; a receiver container which receives an extracted sample discharged from the cartridge holding container, a waste container which receives waste discharged from the cartridge holding container, and a waste port which discharges the waste received by the waste container.

5. The pretreatment apparatus according to claim 4, wherein the extraction solution receiver mechanism is disposed under the cartridge transfer means and wherein the relative position changing mechanism changes a relative position between the extraction solution receiver mechanism and the cartridge transfer means.

6. The pretreatment apparatus according to claim 2, wherein the pressurizing section applies pressure to any cartridge holding container shifted in an action range of the pressurizing section by the relative position changing mechanism which changes a relative position between the pressurizing section and the cartridge holding container.

7. The pretreatment apparatus according to claim 1, wherein the pressurizing section is disposed above the cartridge transfer means and pressurizes the selected cartridge holding container which is positioned under the pressurizing section.

8. The pretreatment apparatus according to claim 7, wherein a plurality of the pressurizing sections are arranged and positioned where the pressurizing sections apply pressure to the cartridge transfer means and are symmetrical with respect to a center of the cartridge transfer means.

9. The pretreatment apparatus according to claim 2, wherein the relative position changing mechanism shifts the cartridge transfer means and the extraction solution receiver mechanism in a direction in which they reach a next operational position in the shortest period of time.

10. The pretreatment apparatus according to claim 1, wherein a CCD camera is installed outside at least one of the cartridge transfer means and the extraction solution receiver mechanism.

11. The pretreatment apparatus according to claim 10, wherein a position of a receiver container of said extraction solution receiver mechanism for receiving an extraction sample and a waste container for receiving waste are switched in accordance with an amount of the sample solution detected in the receiver container by the CCD camera by rotation of said cartridge transfer means.

12. The pretreatment apparatus according to claim 1, further comprising:
    a housing section replacement mechanism for replacing a selected one of the plurality of cartridge holding containers with a new cartridge holding container for each completion of a pretreatment and including a cartridge holding container storage section and a cartridge holding container transfer arm.

13. The pretreatment apparatus according to claim 1, further comprising:
    a separating agent replacement mechanism for replacing a solid-phase extraction cartridge with a new solid-phase extraction cartridge for each completion of a pretreatment and including a solid-phase extraction cartridge storage section and a solid-phase extraction cartridge transfer arm.

14. An analyzer comprising, in addition to the pretreatment apparatus according to claim 1,
    a transporting mechanism for transporting an extraction sample obtained by the pretreatment apparatus to an ionizing section;
    wherein the ionizing section ionizes the extraction sample;
    a mass spectrometric section for analyzing the extraction sample ionized by the ionizing section; and whereby
    the automatic control section automatically controls the operation of the analyzer.

15. The analyzer according to claim 14,
    wherein a separation column is provided before the ionizing section.

16. The analyzer according to claim 15,
    wherein a plurality of separation columns, which comprise at least one of reversed-phase columns, normal-phase columns, cation exchange columns and anion exchange columns, and which precede the ionizing section, are multiplexed in a revolver configuration.

* * * * *